United States Patent
Lin et al.

(10) Patent No.: US 7,342,128 B2
(45) Date of Patent: *Mar. 11, 2008

(54) METHOD FOR OXIDIZING A SLURRY COMPOSITION IN A POST OXIDATION ZONE IN THE PRESENCE OF ADDED STEAM

(75) Inventors: Robert Lin, Kingsport, TN (US); Marcel de Vreede, Barendrecht (NL); Johannes Wilhelmus Sluijmers, Barendrecht (NL); Martin De Boer, Barendrecht (NL); Thomas Earl Woodruff, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/254,406

(22) Filed: Oct. 20, 2005

(65) Prior Publication Data

US 2006/0084824 A1    Apr. 20, 2006

Related U.S. Application Data

(63) Continuation-in-part of application No. 10/423,389, filed on Apr. 25, 2003.

(51) Int. Cl.
*C07C 51/16* (2006.01)
*C07C 51/42* (2006.01)

(52) U.S. Cl. .................... 562/485; 562/417; 562/421; 562/486

(58) Field of Classification Search ................. 562/416, 562/485, 486, 487, 417, 421
See application file for complete search history.

(56) References Cited

U.S. PATENT DOCUMENTS 3,057,909 A    10/1962    Sebelist et al.
3,064,044 A    11/1962    Baldwin (Continued)

FOREIGN PATENT DOCUMENTS

EP    0111784 B1    2/1986

(Continued)

OTHER PUBLICATIONS

USPTO Office Action dated Nov. 22, 2005 for U.S. Appl. No. 10/161,571.

(Continued)

*Primary Examiner*—Taylor Victor Oh
(74) *Attorney, Agent, or Firm*—Steven A. Owen; Bernard J. Graves, Jr.

(57) ABSTRACT

The present invention relates to a process for oxidizing a slurry composition in a post oxidation zone in the presence of added steam. More specifically, the present invention relates to a process for oxidizing a crude terephthalic acid composition in a post oxidation zone in the presence of added steam in a process for the production of a crystallized post oxidation composition.

16 Claims, 3 Drawing Sheets

U.S. PATENT DOCUMENTS

| | | | |
|---|---|---|---|
| 3,452,088 | A | 6/1969 | Olsen et al. |
| 3,584,039 | A | 6/1971 | Meyer |
| 3,850,983 | A | 11/1974 | Park |
| 3,931,305 | A | 1/1976 | Fisher |
| 3,996,271 | A | 12/1976 | Yokota et al. |
| 4,158,738 | A | 6/1979 | Scott et al. |
| 4,356,319 | A | 10/1982 | Roffia et al. |
| 4,500,732 | A | 2/1985 | Petty-Weeks et al. |
| 4,772,748 | A | 9/1988 | Hashizume et al. |
| 4,892,970 | A | 1/1990 | Nowicki et al. |
| 4,939,297 | A | 7/1990 | Browder et al. |
| 5,095,146 | A | 3/1992 | Zeitlin et al. |
| 5,175,355 | A | 12/1992 | Streich et al. |
| 5,510,521 | A | 4/1996 | McGehee et al. |
| 5,567,842 | A | 10/1996 | Izumisawa et al. |
| 5,583,254 | A | 12/1996 | Turner et al. |
| 5,756,833 | A | 5/1998 | Rosen et al. |
| 6,297,348 | B1 | 10/2001 | Rodden et al. |
| 6,689,903 | B2 | 2/2004 | O'Meadhra et al. |
| 7,161,027 | B2 * | 1/2007 | Sheppard et al. ........... 562/486 |
| 2002/0183546 | A1 | 12/2002 | Sheppard et al. |
| 2002/0193630 | A1 | 12/2002 | Lin et al. |

FOREIGN PATENT DOCUMENTS

| | | | |
|---|---|---|---|
| GB | 983677 | * | 2/1965 |
| GB | 983677 | A | 2/1965 |
| GB | 1152575 | | 5/1969 |
| GB | 1358520 | A | 7/1974 |
| GB | 1454478 | A | 11/1976 |
| JP | 2001-288139 | A | 10/2001 |
| WO | WO 99/31038 | A1 | 6/1999 |

OTHER PUBLICATIONS

Arun Pal Aneja and Viney Pal Aneja, "The Effect of Water and Air Contamination on Poly(Ethylene Terephthalate) Formation", Polymer Engineering Reviews, 1982, pp. 123-133, vol. 2, No. 2.

V. F. Nazimok et al., "Tere-or Isophthalic Acids," Chemical Abstracts, Mar. 3, 1986, pp. 657, vol. 104, No. 9, Columbus, Ohio.

Copending U.S. Appl. No. 10/161,571 filed May 31, 2002.

Copending U.S. Appl. No. 10/156,312 filed May 28, 2002.

Copending U.S. Appl. No.10/423,389 filed Apr. 25, 2003.

USPTO Office Action dated Oct. 17, 2005 for U.S. Appl. No. 10/156,312.

USPTO Office Action dated Aug. 23, 2005 for U.S. Appl. No. 10/156,312.

USPTO Office Action dated May 27, 2004 for U.S. Appl. No. 10/156,312.

USPTO Office Action dated Apr. 22, 2005 for U.S. Appl. No. 10/156,312.

USPTO Office Action dated Oct. 3, 2003 for U.S. Appl. No. 10/156,312.

USPTO Office Action dated Dec. 4, 2002 for U.S. Appl. No. 10/156,312.

USPTO Office Action dated Nov. 23, 2005 for U.S. Appl. No. 10/423,389.

USPTO Office Action dated Jul. 13, 2005 for U.S. Appl. No. 10/423,389.

USPTO Office Action dated Feb. 7, 2005 for U.S. Appl. No. 10/423,389.

USPTO Office Action dated Jun. 30, 2004 for U.S. Appl. No. 10/423,389.

USPTO Office Action dated Jun. 29, 2005 for U.S. Appl. No. 10/161,571.

USPTO Office Action dated Sep. 9, 2004 for U.S. Appl. No. 10/161,571.

USPTO Office Action dated Apr. 23, 2004 for U.S. Appl. No. 10/161,571.

USPTO Office Action dated Sep. 24, 2003 for U.S. Appl. No. 10/161,571.

USPTO Office Action dated Dec. 4, 2002 for U.S. Appl. No. 10/161,571.

USPTO office action dated Jul. 17, 2006 for copending U.S. Appl. No. 10/161,571.

USPTO Office Action dated Jul. 17, 2007 for copending U.S. Appl. No. 10/156,312.

USPTO Office Action dated Oct. 19, 2006 for copending U.S. Appl. No. 10/156,312.

USPTO Office Action dated Jun. 1, 2006 for copending U.S. Appl. No. 10/156,312.

Copending U.S. Appl. No. 11/254,406 filed Oct. 20, 2005.

Copending U.S. Appl. No. 10/423,389 filed Apr. 25, 2003.

* cited by examiner

METHOD FOR OXIDIZING A SLURRY COMPOSITION IN A POST OXIDATION ZONE IN THE PRESENCE OF ADDED STEAM

CROSS REFERENCE TO RELATED APPLICATION

This application is a continuation-in-part of copending U.S. application Ser. No. 10/423,389, filed Apr. 25, 2003, hereby incorporated by reference in its entirety to the extent that it does not contradict statements herein.

FIELD OF INVENTION

The present invention relates to a process for oxidizing a slurry composition in a post oxidation zone in the presence of added steam. More specifically, the present invention relates to a process for oxidizing a crude terephthalic acid composition in a post oxidation zone in the presence of added steam in a process for the production of a crystallized post oxidation composition.

BACKGROUND OF THE INVENTION

Terephthalic acid (TPA) is commercially produced by oxidation of para-xylene in the presence of a catalyst, such as, for example, Co, Mn, Br and a solvent. Terephthalic acid used in the production of polyester fibers, films, and resins must be further treated to remove impurities present due to the initial oxidation of para-xylene. Some commercial processes remove impurities by isolating a crude terephthalic acid solid, dissolving the solid in water at high temperatures and pressures, hydrogenating the resultant solution, cooling and crystallizing the terephthalic acid product out of solution, and separating the solid terephthalic product from the liquid as discussed in U.S. Pat. No. 3,584,039, herein incorporated by reference. Colored impurities from the benzil, anthraquinone, and fluorenone families are hydrogenated to colorless products and leave the process with the terephthalic acid solid product and wastewater streams.

Still other methods of obtaining a terephthalic acid product suitable as starting material for the production of polyesters do not involve a hydrogenation step. A method of producing a terephthalic acid product suitable for polyester production is to completely or nearly completely react para-xylene in a multiple stage oxidation process.

In an embodiment of this invention, a unique and novel process is provided wherein a crude carboxylic acid composition is produced by the oxidation of an aromatic feedstock, typically p-xylene, and is further oxidized in a multiple step process in the presence of added steam in a post oxidation zone.

In an embodiment of the invention, the addition of steam to a post oxidation zone subsequent to the primary oxidation zone results in a higher quality post oxidation composition compared to conventional techniques. This is not intuitive because the oxidation process actually produces water, and the current practice has been to minimize that production of water in the oxidation process; and it is not recognized that using added steam in the post oxidation zone would also produce a product of low color.

SUMMARY OF THE INVENTION

This invention provides a process to produce a crystallized post oxidation composition from a crude carboxylic acid slurry by injecting steam in a post oxidation zone subsequent to the primary oxidation zone.

In a first embodiment of this invention, a process to produce a post oxidation composition is provided comprising:

(a) oxidizing an aromatic feedstock in a primary oxidation zone to form a crude carboxylic acid composition;

(b) optionally routing the crude carboxylic acid composition in a solid liquid displacement zone to form a slurry composition;

(c) oxidizing in a post oxidation zone the crude carboxylic acid composition or the slurry composition in the presence of added steam to form the post oxidation composition; wherein the post oxidation zone comprises at least one post oxidation device; wherein the crude carboxylic acid composition comprises at least one carboxylic acid; where said post oxidation composition has a b* color less than said slurry composition or said crude carboxylic acid composition.

In another embodiment of this invention, a process to produce a crystallized post oxidation composition is provided. The process comprising the following steps:

(a) oxidizing an aromatic feedstock at a temperature of about 110° C. to about 200° C. in a primary oxidation zone to form a crude carboxylic acid composition;

(b) optionally routing impurities from the crude carboxylic acid composition in a solid liquid displacement zone to form a slurry composition;

(c) oxidizing the crude carboxylic composition or the slurry composition in a post oxidation zone in the presence of added steam to form a post oxidation composition; wherein the post oxidation zone comprises at least one post oxidation device; wherein the pressure of the post oxidation device is operated between about 10 barg to about 50 barg; and (d) crystallizing in a crystallization zone the post oxidation composition to form the crystallized post oxidation composition; wherein the crystallization zone comprises at least one crystallizer; wherein the crystallizer is operated at a temperature between about 140° C. and 190° C.; and wherein the crystallized post oxidation composition has a b* color of less than 4.5.

In another embodiment of this invention, a process to produce a purified post oxidation composition is provided. The process comprising the following steps:

(a) oxidizing an aromatic feedstock at a temperature of about 110° C. to about 200° C. in a primary oxidation zone to form a crude carboxylic acid composition;

(b) routing the crude carboxylic acid composition in a solid liquid displacement zone to form a slurry composition;

(c) oxidizing in a post oxidation zone the crude carboxylic acid composition or the slurry composition in the presence of added steam to form the post oxidation composition; wherein the post oxidation zone comprises at least one post oxidation device; wherein the crude carboxylic acid composition comprises at least one carboxylic acid;

(d) purifying the post oxidation composition in a purification zone to form the purified post oxidation composition having b* color less than said post oxidation composition.

These embodiments, and other embodiments, will become more apparent to others with ordinary skill in the art after reading this disclosure.

DETAILED DESCRIPTION OF THE INVENTION

The present invention may be understood more readily by reference to the following detailed description of preferred embodiments of the invention and the Example included therein and to the Figures and their previous and following description.

Before the present compounds, compositions, articles, devices, and/or methods are disclosed and described, it is to be understood that this invention is not limited to specific synthetic methods, specific processes, or to particular apparatuses, as such may, of course, vary. It is also to be understood that the terminology used herein is for the purpose of describing particular embodiments only and is not intended to be limiting.

In this specification and in the claims, which follow, reference will be made to a number of terms which shall be defined to have the following meanings:

As used in the specification and the appended claims, the singular forms "a," "an" and "the" include plural referents unless the context clearly dictates otherwise. Thus, for example, reference to a post oxidation device includes one or more post oxidation device(s).

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where the event or circumstance occurs and instances where it does not. For example, the phrase "optionally heated" means that the material may or may not be heated and that such phrase includes both heated and unheated processes.

Throughout this application, where patents or publications are referenced, the disclosures of these references in their entireties are intended to be incorporated by reference into this application to the extent that they do not contradict statements made herein, in order to more fully describe the state of the art to which the invention pertains.

Reference will now be made in detail to the present preferred embodiment(s) of the invention, examples of which are illustrated in the accompanying drawings. Wherever possible, the same reference numbers are used throughout the drawings to refer to the same or like parts.

Figure 1:
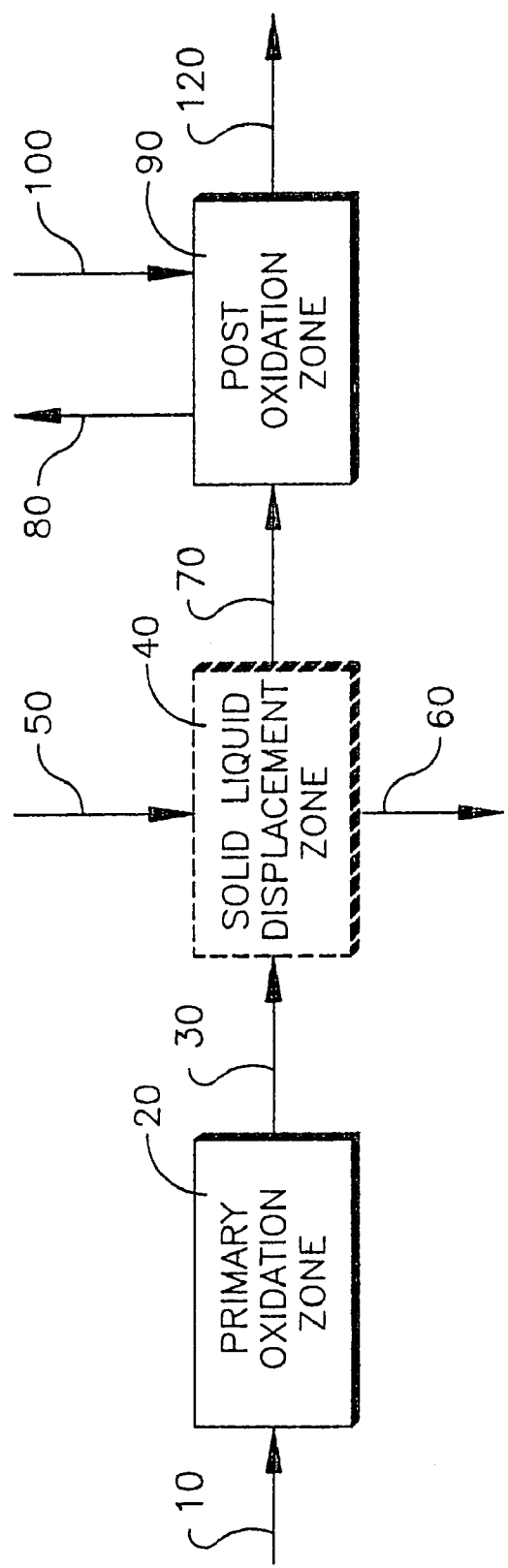
FIG. 1 is a schematic of a process for oxidizing an aromatic feed stock 10 and then subsequently oxidizing a slurry composition 70 or a crude carboxylic acid composition 30 in a post oxidation zone 90 in the presence of added steam 100 to produce a post oxidation composition 90.

In a first embodiment of this invention, a process to produce a post oxidation composition 120 is provided is FIG. 1. The process comprises:

(a) oxidizing an aromatic feedstock 10 in a primary oxidation zone 20 to form a crude carboxylic acid composition 30;

(b) routing said crude carboxylic acid composition 30 in a solid liquid displacement zone 40 to form a slurry composition 70;

(c) oxidizing in a post oxidation zone 90 a crude carboxylic acid composition 30 or slurry composition 70 in the presence of added steam 100 to form the post oxidation composition 120 and an offgas stream 80; wherein the post oxidation zone 90 comprises at least one post oxidation device; wherein the carboxylic acid composition 30 comprises at least one carboxylic acid; and wherein the post oxidation composition 120 has a b* color of less than 4.5.

The primary oxidation zone 20, the solid liquid displacement zone 40 and the post oxidation zone 90 are described subsequently in this disclosure.

Figure 2:
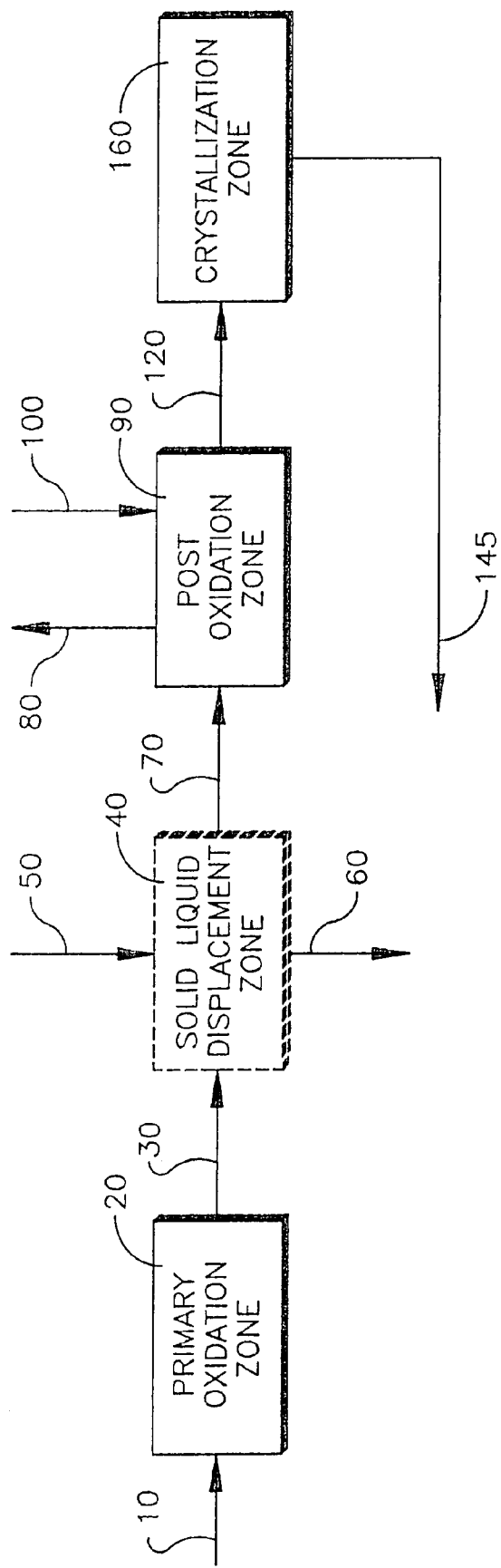
FIG. 2 is a schematic of a process for oxidizing an aromatic feed stock 10 and then subsequently oxidizing a slurry composition 70 or a crude carboxylic acid composition 30 in a post oxidation zone 90 in the presence of added steam 100 to produce a post oxidation composition 120 followed by crystallizing in an crystallization zone 160.

In another embodiment of the invention, a process to produce a crystallized post oxidation composition 145 is provided as shown in FIG. 2. The process comprises the following steps.

Step (a) comprises oxidizing an aromatic feedstock 10 in a primary oxidation zone 20 to form a crude carboxylic acid composition 30. The aromatic feedstock 10 comprises at least one oxidizable compound, at least one solvent, and at least one catalyst.

One embodiment of the present invention concerns the liquid-phase partial oxidation of an oxidizable compound. Such oxidation is preferably carried out in the liquid phase of a multi-phase reaction medium contained in an agitated reactor. Suitable agitated reactors include, for example, bubble-agitated reactors (e.g., bubble column reactors) and mechanically agitated reactors (e.g., continuous stirred tank reactors). The liquid-phase oxidation is preferably carried out in a bubble column reactor.

As used herein, the term "bubble column reactor" shall denote a reactor for facilitating chemical reactions in a multi-phase reaction medium, wherein agitation of the reaction medium is provided primarily by the upward movement of gas bubbles through the reaction medium. As used herein, the term "agitation" shall denote work dissipated into the reaction medium causing fluid flow and/or mixing. As used herein, the terms "majority", "primarily", and "predominantly" shall mean more than 50 percent.

The oxidizable compound present in the aromatic feed stock 10 preferably comprises at least one hydrocarbyl group. More preferably, the oxidizable compound is an aromatic compound. Still more preferably, the oxidizable compound is an aromatic compound with at least one attached hydrocarbyl group or at least one attached substituted hydrocarbyl group or at least one attached heteroatom or at least one attached carboxylic acid function (—COOH). Even more preferably, the oxidizable compound is an aromatic compound with at least one attached hydrocarbyl group or at least one attached substituted hydrocarbyl group with each attached group comprising from 1 to 5 carbon atoms. Yet still more preferably, the oxidizable compound is an aromatic compound having exactly two attached groups with each attached group comprising exactly one carbon atom and consisting of methyl groups and/or substituted methyl groups and/or at most one carboxylic acid group. Even still more preferably, the oxidizable compound is para-xylene, meta-xylene, para-tolualdehyde, meta-tolualdehyde, para-toluic acid, meta-toluic acid, and/or acetaldehyde. Most preferably, the oxidizable compound is para-xylene.

A "hydrocarbyl group", as defined herein, is at least one carbon atom that is bonded only to hydrogen atoms or to other carbon atoms. A "substituted hydrocarbyl group", as defined herein, is at least one carbon atom bonded to at least one heteroatom and to at least one hydrogen atom. "Heteroatoms", as defined herein, are all atoms other than carbon and hydrogen atoms. "Aromatic compounds", as defined herein, comprise an aromatic ring, preferably having at least 6 carbon atoms, even more preferably having only carbon atoms as part of the ring. Suitable examples of such aromatic rings include, but are not limited to, benzene, biphenyl, terphenyl, naphthalene, and other carbon-based fused aromatic rings.

Suitable examples of the oxidizable compound include aliphatic hydrocarbons (e.g., alkanes, branched alkanes, cyclic alkanes, aliphatic alkenes, branched alkenes, and cyclic alkenes); aliphatic aldehydes (e.g., acetaldehyde, propionaldehyde, isobutyraldehyde, and n-butyraldehyde); aliphatic alcohols (e.g., ethanol, isopropanol, n-propanol, n-butanol, and isobutanol); aliphatic ketones (e.g., dimethyl ketone, ethyl methyl ketone, diethyl ketone, and isopropyl methyl ketone); aliphatic esters (e.g., methyl formate, methyl acetate, ethyl acetate); aliphatic peroxides, peracids, and hydroperoxides (e.g., t-butyl hydroperoxide, peracetic acid, and di-t-butyl hydroperoxide); aliphatic compounds with groups that are combinations of the above aliphatic species plus other heteroatoms (e.g., aliphatic compounds comprising one or more molecular segments of hydrocarbons, aldehydes, alcohols, ketones, esters, peroxides, peracids, and/or hydroperoxides in combination with sodium, bromine, cobalt, manganese, and zirconium); various benzene rings, naphthalene rings, biphenyls, terphenyls, and other aromatic groups with one or more attached hydrocarbyl groups (e.g., toluene, ethylbenzene, isopropylbenzene, n-propylbenzene, neopentylbenzene, para-xylene, meta-xylene, ortho-xylene, all isomers of trimethylbenzenes, all isomers of tetramethylbenzenes, pentamethylbenzene, hexamethylbenzene, all isomers of ethyl-methylbenzenes, all isomers of diethylbenzenes, all isomers of ethyl-dimethylbenzenes, all isomers of dimethylnaphthalenes, all isomers of ethyl-methylnaphthalenes, all isomers of diethylnaphthalenes, all isomers of dimethylbiphenyls, all isomers of ethyl-methylbiphenyls, and all isomers of diethylbiphenyls, stilbene and with one or more attached hydrocarbyl groups, fluorene and with one or more attached hydrocarbyl groups, anthracene and with one or more attached hydrocarbyl groups, and diphenylethane and with one or more attached hydrocarbyl groups); various benzene rings, naphthalene rings, biphenyls, terphenyls, and other aromatic groups with one or more attached hydrocarbyl groups and/or one or more attached heteroatoms, which may connect to other atoms or groups of atoms (e.g., phenol, all isomers of methylphenols, all isomers of dimethylphenols, all isomers of naphthols, benzyl methyl ether, all isomers of bromophenols, bromobenzene, all isomers of bromotoluenes including alpha-bromotoluene, dibromobenzene, cobalt naphthenate, and all isomers of bromobiphenyls); various benzene rings, naphthalene rings, biphenyls, terphenyls, and other aromatic groups with one or more attached hydrocarbyl groups and/or one or more attached heteroatoms and/or one or more attached substituted hydrocarbyl groups (e.g., benzaldehyde, all isomers of bromobenzaldehydes, all isomers of brominated tolualdehydes including all isomers of alpha-bromo-tolualdehydes, all isomers of hydroxybenzaldehydes, all isomers of bromo-hydroxybenzaldehydes, all isomers of benzene dicarboxaldehydes, all isomers of benzene tricarboxaldehydes, para-tolualdehyde, meta-tolualdehyde, ortho-tolualdehyde, all isomers of toluene dicarboxaldehydes, all isomers of toluene tricarboxaldehydes, all isomers of toluene tetracarboxaldehydes, all isomers of dimethylbenzene dicarboxaldehydes, all isomers of dimethylbenzene tricarboxaldehydes, all isomers of dimethylbenzene tetracarboxaldehydes, all isomers of trimethylbenzene tricarboxaldehydes, all isomers of ethyltolualdehydes, all isomers of trimethylbenzene dicarboxaldehydes, tetramethylbenzene dicarboxaldehyde, hydroxymethyl-benzene, all isomers of hydroxymethyl-toluenes, all isomers of hydroxymethyl-bromotoluenes, all isomers of hydroxymethyl-tolualdehydes, all isomers of hydroxymethyl-bromotolualdehydes, benzyl hydroperoxide, benzoyl hydroperoxide, all isomers of tolyl methyl-hydroperoxides, and all isomers of methylphenol methyl-hydroperoxides); various benzene rings, naphthalenes rings, biphenyls, terphenyls, and other aromatic groups with one or more attached selected groups, selected groups meaning hydrocarbyl groups and/or attached heteroatoms and/or substituted hydrocarbyl groups and/or carboxylic acid groups and/or peroxy acid groups (e.g., benzoic acid, para-toluic acid, meta-toluic acid, ortho-toluic acid, all isomers of ethylbenzoic acids, all isomers of propylbenzoic acids, all isomers of butylbenzoic acids, all isomers of pentylbenzoic acids, all isomers of dimethylbenzoic acids, all isomers of ethylmethylbenzoic acids, all isomers of trimethylbenzoic acids, all isomers of tetramethylbenzoic acids, pentamethylbenzoic acid, all isomers of diethylbenzoic acids, all isomers of benzene dicarboxylic acids, all isomers of benzene tricarboxylic acids, all isomers of methylbenzene dicarboxylic acids, all isomers of dimethylbenzene dicarboxylic acids, all isomers of methylbenzene tricarboxylic acids, all isomers of bromobenzoic acids, all isomers of dibromobenzoic acids, all isomers of bromotoluic acids including alpha-bromotoluic acids, tolyl acetic acid, all isomers of hydroxybenzoic acid isomerss, all isomers of hydroxymethyl-benzoic acids, all isomers of hydroxytoluic acids, all isomers of hydroxymethyl-toluic acids, all isomers of hydroxymethyl-benzene dicarboxylic acids, all isomers of hydroxybromobenzoic acids, all isomers of hydroxybromotoluic acids, all isomers of hydroxymethyl-bromobenzoic acids, all isomers of carboxy benzaldehydes, all isomers of dicarboxy benzaldehydes, perbenzoic acid, all isomers of hydroperoxymethyl-benzoic acids, all isomers of hydroperoxymethyl-hydroxybenzoic acid isomerss, all isomers of hydroperoxycarbonyl-benzoic acids, all isomers of hydroperoxycarbonyl-toluenes, all isomers of methylbiphenyl carboxylic acids, all isomers of dimethylbiphenyl carboxylic acids, all isomers of methylbiphenyl dicarboxylic acids, all isomers of biphenyl tricarboxylic acids, all isomers of stilbene with one or more attached selected groups, all isomers of fluorenone with one or more attached selected groups, all isomers of naphthalene with one or more attached selected groups, benzil, all isomers of benzil with one or more attached selected groups, benzophenone, all isomers of benzophenone with one or more attached selected groups, anthraquinone, all isomers of anthraquinone with one or more attached selected groups, all isomers of diphenylethane with one or more attached selected groups, benzocoumarin, and all isomers of benzocoumarin with one or more attached selected groups).

It should be understood that the oxidizable compound present in the liquid-phase feed may comprise a combination of two or more different oxidizable chemicals. These two or more different chemical materials can be fed commingled in the aromatic feedstock 10 or may be fed separately in multiple feed streams. For example, an aromatic feed stock 10 comprising para-xylene, meta-xylene, para-tolualdehyde, para-toluic acid, and acetaldehyde may be fed to the reactor via a single inlet or multiple separate inlets.

The solvent present in the aromatic feed stock 10 preferably comprises an acid component and a water component. The solvent is preferably present in the aromatic feedstock 10 at a concentration in the range of from about 60 to about 98 weight percent, more preferably in the range of from about 80 to about 96 weight percent, and most preferably in the range of from 85 to 94 weight percent. The acid component of the solvent is preferably an organic low molecular weight monocarboxylic acid having 1-6 carbon atoms, more preferably 2 carbon atoms. Most preferably, the acid component of the solvent is acetic acid. Preferably, the acid component makes up at least about 75 weight percent of the solvent, more preferably at least about 80 weight percent of the solvent, and most preferably 85 to 98 weight percent of the solvent, with the balance being water.

Suitable solvents include, but are not limited to, aliphatic mono-carboxylic acids, preferably containing 2 to 6 carbon atoms, or benzoic acid and mixtures thereof and mixtures of these compounds with water.

The catalyst system present in the aromatic feed stock 10 is preferably a homogeneous, liquid-phase catalyst system capable of promoting oxidation (including partial oxidation) of the oxidizable compound. More preferably, the catalyst system comprises at least one multi-valent transition metal. Still more preferably, the multi-valent transition metal comprises cobalt. Even more preferably, the catalyst system comprises cobalt and bromine. Most preferably, the catalyst system comprises cobalt, bromine, and manganese.

When cobalt is present in the catalyst system, it is preferred for the amount of cobalt present in the aromatic feedstock 10 to be such that the concentration of cobalt in the liquid phase of the reaction medium in the primary oxidation zone 20 is maintained in the range of from about 300 to about 6,000 parts per million by weight (ppmw), more preferably in the range of from about 700 to about 4,200 ppmw, and most preferably in the range of from 1,200 to 3,000 ppmw. When bromine is present in the catalyst system, it is preferred for the amount of bromine present in the aromatic feedstock 10 to be such that the concentration of bromine in the liquid phase of the reaction medium is maintained in the range of from about 300 to about 5,000 ppmw, more preferably in the range of from about 600 to about 4,000 ppmw, and most preferably in the range of from 900 to 3,000 ppmw. When manganese is present in the catalyst system, it is preferred for the amount of manganese present in the aromatic feedstock 10 to be such that the concentration of manganese in the liquid phase of the reaction medium is maintained in the range of from about 20 to about 1,000 ppmw, more preferably in the range of from about 40 to about 500 ppmw, most preferably in the range of from 50 to 200 ppmw.

The concentrations of the cobalt, bromine, and/or manganese in the liquid phase of the reaction medium, provided above, are expressed on a time-averaged and volume-averaged basis. As used herein, the term "time-averaged" shall denote an average of at least 10 measurements taken over a continuous 100 second period of time. As used herein, the term "volume-averaged" shall denote an average of at least 10 measurements taken at uniform 3-dimensional spacings throughout a certain volume.

The weight ratio of cobalt to bromine (Co:Br) in the catalyst system introduced into the primary oxidation zone 20 is preferably in the range of from about 0.25:1 to about 4:1, more preferably in the range of from about 0.5:1 to about 3:1, and most preferably in the range of from 0.75:1 to 2:1. The weight ratio of cobalt to manganese (Co:Mn) in the catalyst system introduced into the primary oxidation zone 20 is preferably in the range of from about 0.3:1 to about 40:1, more preferably in the range of from about 5:1 to about 30:1, and most preferably in the range of from 10:1 to 25:1.

The aromatic feedstock 10 introduced into the primary oxidation zone 10 can include small quantities of compounds such as, for example, toluene, ethylbenzene, 4-carboxybenzaldehyde (4-CBA), benzoic acid, para-toluic acid, para-toluic aldehyde, alpha bromo para-toluic acid, isophthalic acid, phthalic acid, trimellitic acid, polyaromatics, and/or suspended particulate. In an embodiment of the invention, when bubble column reactor is employed for the production of terephthalic acid, meta-xylene and ortho-xylene are also considered impurities. It is preferred that the total amount of impurities in the aromatic feedstock 10 introduced into bubble column reactor is less than about 3 weight percent.

Step (b) optionally comprises routing a crude carboxylic acid composition 30 in a solid liquid displacement zone 40 to form a slurry composition 70.

The crude carboxylic acid composition 30 comprises at least one carboxylic acid, at least one catalyst, at least one solvent, and impurities. The impurities typically comprise one or more of the following compounds: 4-carboxybenzaldehyde(4-CBA), trimellitic acid(TMA), and 2,6-dicarboxyfluorenone(2,6-DCF). The solvent typically comprises acetic acid, but can be any solvent that has been previously mentioned.

The crude carboxylic acid composition 30 is produced by oxidizing in a primary oxidation zone 20 an aromatic feed stock 10. In one embodiment, the aromatic feedstock 10 comprises para-xylene. The primary oxidation zone 20 comprises at least one oxidation reactor. The crude carboxylic acid composition 30 comprises at least one carboxylic acid.

In an embodiment of the invention, the oxidation reactor can be operated at temperatures between about 110° C. to about 200° C., preferably about 140° C. to about 170° C. Typically, the oxidizable compound in the aromatic feedstock 10 is para-xylene, and the carboxylic acid produced is terephthalic acid. In one embodiment of the invention, the primary oxidation zone 20 comprises a bubble column.

Carboxylic acids include aromatic carboxylic acids produced via controlled oxidation of an organic substrate or any carboxylic acid produced by the oxidation of oxidizable compounds previously mentioned. Such aromatic carboxylic acids include compounds with at least one carboxylic acid group attached to a carbon atom that is part of an aromatic ring, preferably having at least 6 carbon atoms, even more preferably having only carbon atoms. Suitable examples of such aromatic rings include, but are not limited to, benzene, biphenyl, terphenyl, naphthalene, and other carbon-based fused aromatic rings. Examples of suitable carboxylic acids include, but are not limited to, terephthalic acid, benzoic acid, p-toluic, isophthalic acid, trimellitic acid, naphthalene dicarboxylic acid, and 2,5-diphenyl-terephthalic acid.

Crude terephthalic acid composition is conventionally synthesized via the liquid phase oxidation of para-xylene in the presence of suitable oxidation catalyst. In another embodiment of the invention, suitable catalysts include, but are not limited to, cobalt, manganese and bromine compounds, which are soluble in the selected solvent.

The crude carboxylic acid composition in conduit 30 is fed to a solid liquid displacement zone 40 capable of removing a portion of the liquid contained in the crude carboxylic acid composition 30 to produce the slurry composition in conduit 70. In an embodiment of the invention, a portion means at least 5% by weight of the liquid is removed. In another embodiment of the invention, a portion means at least 10% by weight of the liquid is removed. In another embodiment of the invention, a portion means at least 15% by weight of the liquid is removed. In another embodiment of the invention, a portion means at least 25% by weight of the liquid is removed. In another embodiment of the invention, a portion means at least 35% by weight of the liquid is removed. In another embodiment of the invention, a portion means at least 45% by weight of the liquid is removed. In another embodiment of the invention, a portion means at least 55% by weight of the liquid is removed. In another embodiment of the invention, a portion means at least 65% by weight of the liquid is removed. In another embodiment of the invention, a portion means at least 75% by weight of the liquid is removed. In another embodiment of the invention, a portion means at least 85% by weight of the liquid is removed. In another embodiment of the invention, a portion can mean any part up to and including the whole by weight of the liquid is removed.

The removal of a portion of the liquid to produce a slurry composition in conduit 70 can be accomplished by any means known in the art. Typically, the solid liquid displacement zone 40 comprises a solid-liquid separator that is selected from the group consisting of a decanter centrifuge, rotary disk centrifuge, belt filter, rotary vacuum filter, and the like. The crude carboxylic acid composition in conduit 30 is fed to the solid liquid displacement zone 40 comprising a solid-liquid separator. In an embodiment of the invention, the solid-liquid separator is operated at temperatures between about 50° C. to about 200° C., or another range is about 140° C. to about 170° C. The solid-liquid separator is operated at pressures between about 30 psig to about 200 psig. The solid-liquid separator in the solid liquid displacement zone 40 may be operated in continuous or batch mode, although it will be appreciated that for commercial processes, the continuous mode is preferred.

The impurities are displaced from the solid liquid displacement zone 40 in a mother liquor and withdrawn via line 60. In one embodiment of the invention, additional solvent is fed to the solid liquid displacement zone 40 via line 50 to reslurry the crude carboxylic acid composition 30 and form a slurry composition 70. The mother liquor 60 is withdrawn from solid liquid displacement zone 40 via line 60 and comprises a solvent, typically acetic acid, catalyst, and bromine compounds. The mother liquor in line 60 may either be sent to a process for separating impurities from oxidation solvent via lines not shown or recycled to the catalyst system via lines not shown. One technique for impurity removal from the mother liquor 60 commonly used in the chemical processing industry is to draw out or "purge" some portion of the recycle stream. Typically, the purge stream is simply disposed of or, if economically justified, subjected to various treatments to remove undesired impurities while recovering valuable components. Examples of impurity removal processes include U.S. Pat. No. 4,939,297 and U.S. Pat. No. 4,356,319, herein incorporated by reference to the extent that they do not contradict statements made herein.

It should be pointed out that the solid liquid displacement zone 40 is optional and also can be located in multiple locations.

Step (c) comprises oxidizing the crude carboxylic acid composition 30 or slurry composition 70 in a post oxidation zone 90 in the presence of added steam 100 to form a post oxidation composition 120. In an embodiment of the invention, the crude carboxylic acid slurry 30 is produced by oxidizing in a primary oxidation zone 20 an aromatic feed stock 10.

The oxidizing in the primary oxidation zone 20 is completed under reaction conditions, which produces a crude carboxylic acid composition 30 from an aromatic feedstock 10. Typically, the crude carboxylic acid composition 30 comprises at least one carboxylic acid. In an embodiment of the invention, the carboxylic acid is terephthalic acid.

Therefore, when terephthalic acid is utilized, the crude carboxylic acid composition 30 would be referred to as crude terephthalic acid composition. However, suitable carboxylic acids include, but are not limited to, terephthalic acid, isophthalic acid, naphthalene dicarboxylic acid, and mixtures thereof. Crude terephthalic acid slurry is conventionally synthesized via the liquid phase oxidation of para-xylene in the presence of metal oxidation catalyst. Suitable catalysts include, but are not limited to, cobalt, manganese and bromide compounds, which are soluble in the selected solvent. Suitable solvents include, but are not limited to, aliphatic mono-carboxylic acids, preferably containing 2 to 6 carbon atoms, or benzoic acid and mixtures thereof and mixtures of these compounds with water. Preferably, the solvent is acetic acid mixed with water in a ratio of about 5:1 to about 25:1, preferably between about 10:1 and about 15:1. However, it should be appreciated that other suitable solvents, such as those disclosed herein, may also be utilized. Patents disclosing the production of terephthalic acid, such as U.S. Pat. Nos. 4,158,738 and 3,996,271, are hereby incorporated by reference.

In an embodiment of the invention where the carboxylic acid is terephthalic acid, the primary oxidation zone 20 can have a water concentration less than about 10 wt %, and most preferably the water concentration is less than about 7 wt %. The post oxidation zone 90 comprises at least one post oxidation device. In an embodiment of the invention, the post oxidation device is operated at a pressure of about 10 barg (bars gauge) to about 50 barg.

The crude carboxylic acid composition 30 is fed to the post oxidation zone 90. In an embodiment of the invention, the post oxidation device is an oxidation reactor capable of further oxidizing the crude carboxylic acid composition. The term post oxidation means that the oxidation occurs after the primary oxidation zone 20 discussed previously. For example, the post oxidation zone 90 can comprise post oxidation devices in series.

In an embodiment of the invention, the crude carboxylic acid composition 30 in the post oxidation device is heated with added steam 100 to between about 180° C. to about 280° C., preferably between about 190° C. to about 240° C., and most preferably between about 195° C. to about 215° C. and further oxidized with air or a source of molecular oxygen to the post oxidation device to produce a post oxidation composition 120. In an embodiment of the invention, the added steam 100 is added in an amount sufficient to allow for the b* color of the post oxidation composition 120 to be lower than the b* color of the crude carboxylic acid composition 30 and/or slurry composition 70. The temperature is the internal temperature of the post oxidation device. When the post oxidation zone 90 comprises more than one post oxidation device, the temperature can vary within the specified range for each post oxidation device. The added steam 100 can be fed in the post oxidation zone 90 by any means known in the art. In addition to using steam, the post oxidation zone 90 can be heated with acetic acid vapor and/or solvent vapor. For example, a connection can be made for the added steam 100 to be directly fed to the acetic acid vapor line and/or solvent vapor line. In an embodiment of the invention, the added steam 100 could be injected into the oxidation reactor in the post oxidation zone 90 through a sparge ring.

Additional air or molecular oxygen may be fed to the post oxidation zone 90 in an amount necessary to oxidize a substantial portion of the partially oxidized products and 4-carboxybenzaldehyde (4-CBA) in the crude carboxylic acid composition 30 to the corresponding carboxylic acid. Generally, at least 70% by weight of the 4-CBA is converted to terephthalic acid in the post oxidation zone 90. Preferably at least 80% by weight of the 4-CBA is converted to terephthalic acid in the post oxidation zone 90. 4-carboxybenzaldehyde and p-toluic acid in high enough concentrations in the terephthalic acid product can be particularly detrimental to polymerization processes as they act as a chain terminator during the condensation reaction between terephthalic acid and ethylene glycol in the production of PET and can be detrimental to the performance of terephthalic acid hydrogenation processes. Typical terephthalic acid product contains on a weight basis less than 500 parts per million (ppm) 4-carboxybenzaldehyde and less than 250 ppm p-toluic acid. Preferably, the post oxidation zone 90 is operated at a temperature and pressure sufficient that the b* color of the post oxidation composition 120 is less than 4.5. Another range is the b* color of the post oxidation composition 120 is less than 3.5

Step (d) comprises crystallizing the post oxidation composition 120 in the crystallization zone 160 to form a crystallized post oxidation composition 145.

In an embodiment of the invention, the crystallization zone 160 comprises at least one crystallizer In addition, the liquid crystallization offgas is removed from the crystallization zone 160 and can be routed to a recovery system where the solvent is removed and crystallization offgas comprising VOCs and pollutants are burned.

In an embodiment of the invention, the carboxylic acid comprises terephthalic acid. The post oxidation composition 120 from the post oxidation zone 90 is withdrawn via line 120 and fed to a crystallization zone 160 comprising at least one crystallizer where it is cooled to a temperature between about 110° C. to about 190° C. to form a crystallized post oxidation composition 145, preferably to a temperature between about 140° C. to about 180° C., most preferably about 150° C. to about 170° C. In an embodiment of the invention, the b* color of the crystallized post oxidation composition in conduit 145 is less than 4.5. Another range is the crystallized post oxidation composition in conduit 145 has a b* color less than 3.5

Figure 3:
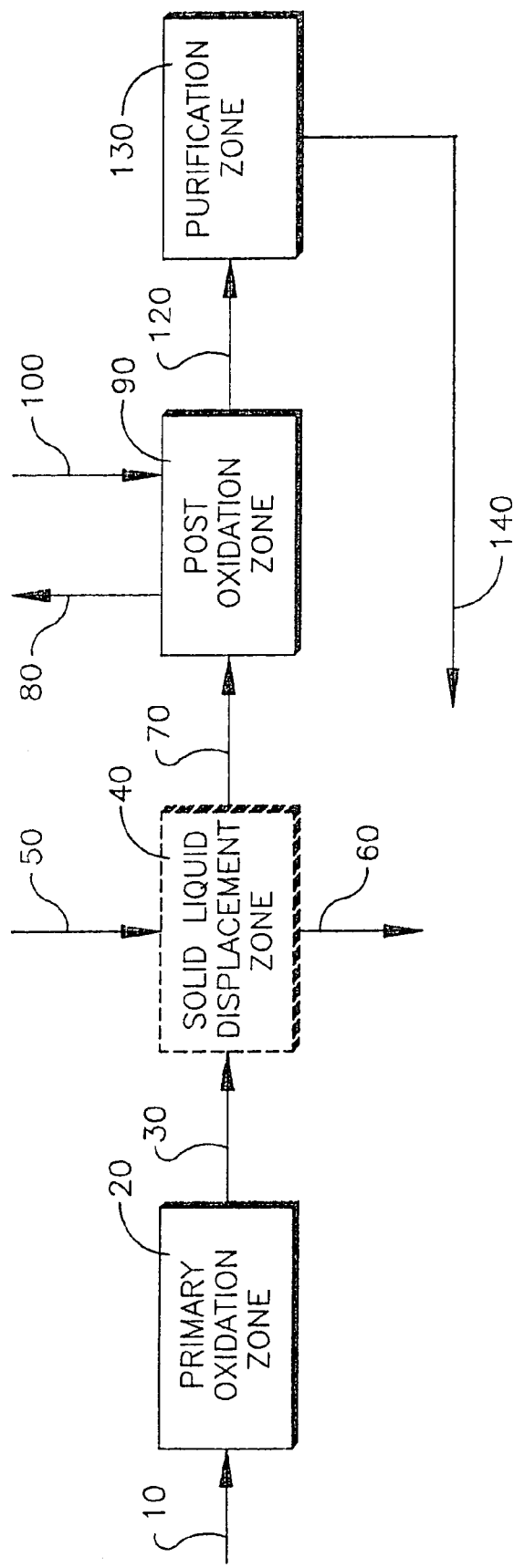
FIG. 3 is a schematic of a process for oxidizing a slurry composition 70 or a crude carboxylic acid composition 30 in a post oxidation zone 90 in the presence of added steam 100 to produce a post oxidation composition 120 followed by directing the post oxidation composition 120 to a purification zone 130 to produced a purified post oxidation composition 140.

In another embodiment of the invention, the post oxidation composition 120 can be purified in a purification zone 130 to form a purified post oxidation composition 140 as shown in FIG. 3.

The purifying of the post oxidation composition 120 can be accomplished by any means known in the art. For example colored impurities from the benzil, anthraquinone, and fluorenone families can be hydrogenated to colorless products. In addition any amount of process steps can be between the post oxidation zone and the purifying of the post oxidation composition 120 and the isolation or recovery of the post oxidation composition 120 if desired.

In an embodiment of the invention, the b* color of the purified post oxidation composition 140 is less than 4.5. In another range, the b* color of the purified post oxidation composition in conduit 140 is less than 3.5. In another range, the b* color in the purified post oxidation composition in conduit 140 is between about 0.5 to about 1.5. The b* color is one of the three-color attributes measured on a spectroscopic reflectance-based instrument. The color can be measured by any device known in the art. A Hunter Ultrascan XE instrument is typically the measuring device. Positive readings signify the degree of yellow (or absorbance of blue), while negative readings signify the degree of blue (or absorbance of yellow).

EXAMPLES

The invention has been described in detail with particular reference to preferred embodiments thereof, but it will be understood that variations and modifications can be effected within the spirit and scope of the invention.

Example 1

In a plant trial, steam was used in the heating of a post oxidation device. The temperature of the post oxidation device was operating at about 195° C. to about 215° C. The airflow was set at a ratio of about 3.8 kg air/ton crude carboxylic acid composition. The steam flow to the post oxidation device was between about 6.5 to about 8.2 metric tons/hour. An overall reduction in energy of 0.3 GJ/ton for producing terephthalic acid was observed. This represents a 5% reduction in energy versus operating without the use of steam to the post oxidation device. The acid burn and decomposition in the post oxidation device decreased due to the injection of steam into the post oxidation device. The acid loss (acetic acid/ton post oxidation composition) dropped about 10%. Therefore, both reduction in energy consumption and acid burn were observed through the use of steam to heat the post oxidation device.

We claim:

1. A process to produce a crystallized post oxidation composition said process comprising the following steps in the order named:
   (a) oxidizing an aromatic feedstock at a temperature of about 110° C. to about 200° C. in a primary oxidation zone in the presence of a catalyst system to form a crude carboxylic acid composition; wherein said catalyst system comprises cobalt;
   (b) routing said crude carboxylic acid composition in a solid liquid displacement zone to form a slurry composition and a mother liquor; wherein at least a portion of said catalyst system in the crude carboxylic acid composition is removed in the mother liquor; wherein additional solvent is fed to said solvent liquid displacement zone;
   (c) oxidizing at a temperature of about 180° C. to about 280° C. in a post oxidation zone said crude carboxylic acid composition or said slurry composition in said post oxidation zone in the presence of added steam to form a post oxidation composition and an offgas stream; wherein said post oxidation zone comprises at least one post oxidation device; wherein said post oxidation composition comprises 4-carboxybenzaldehyde; and wherein said post oxidation zone results in at least 70% by weight conversion of said 4-carboxybenzaldehyde to terephthalic acid; and (d) crystallizing in a crystallization zone said post oxidation composition to form said crystallized post oxidation composition; wherein said crystallization zone comprises at least one crystallizer.

2. The process according to claim 1 wherein said crystallized post oxidation composition has a b* color of less than 3.5.

3. The process according claim 1 wherein said carboxylic acid is selected from the group consisting of terephthalic acid, isophthalic acid, naphthalene dicarboxylic acid, and mixtures thereof.

4. The process according to claim 1 wherein said carboxylic acid is terephthalic acid.

5. The process according to claim 4 wherein said added steam is used to heat the post oxidation device to a temperature in a range from about 180° C. to about 280° C.

6. The process according to claim 5 wherein said post oxidation device is operated at a pressure of about 10 barg to about 50 barg.

7. The process according to claim 4 wherein said crystallizer is operated at a temperature between about 140° C. and 190° C.

8. The process according to claim 1 wherein said aromatic feedstock comprises para-xylene.

9. The process according to claim 1 wherein said solvent is acetic acid.

10. The process according to claim 9 wherein said aromatic feed stock comprises para-xylene.

11. A process to produce a purified post oxidation composition comprising the following steps in the order named:
(a) oxidizing an aromatic feedstock at a temperature of about 110° C. to about 200° C. in a primary oxidation zone in the presence of a catalyst system to form a crude carboxylic acid composition; wherein said catalyst system comprises cobalt;
(b) routing said crude carboxylic acid composition in a solid liquid displacement zone to form a slurry composition; and a mother liquor; wherein at least a portion of said catalyst system in the crude carboxylic acid composition is removed in the mother liquor; wherein additional solvent is fed to said solvent liquid displacement zone;
(c) oxidizing at a temperature of about 180° C. to about 280° C. in a post oxidation zone said crude carboxylic acid composition or said slurry composition in the presence of added steam to form a post oxidation composition; wherein said post oxidation zone comprises at least one post oxidation device; wherein said crude carboxylic acid composition comprises at least one carboxylic acid; wherein said post oxidation composition comprises 4-carboxybenzaldehyde; and wherein said post oxidation zone results in at least 70% by weight conversion of said 4-carboxybenzaldehyde to terephthalic acid and
(d) purifying said post oxidation composition in a purification zone to form said purified post oxidation composition having b* color of less than said post oxidation composition; and wherein said b* is less than 4.5.

12. The process according to claim 11 where said purified post oxidation composition has a b* color less than 3.5.

13. The process according to claim 1 wherein said carboxylic acid is selected from the group consisting of terephthalic acid, isophthalic acid, naphthalene dicarboxylic acid, and mixtures thereof.

14. The process according to claim 1 wherein said carboxylic acid is terephthalic acid.

15. The process according to claim 14 wherein said added steam is used to heat said post oxidation device to a temperature in a range from about 180° C. to about 280° C.

16. The process according to claim 15 wherein said post oxidation device is operated at a pressure of about 10 barg to about 50 barg.

* * * * *